(12) United States Patent
Facey et al.

(10) Patent No.: US 8,470,567 B2
(45) Date of Patent: Jun. 25, 2013

(54) APPARATUS AND PROCESS FOR PRODUCTION OF BIOGAS

(75) Inventors: Roderick Michael Facey, Edmonton (CA); Aaron Stavne, Sherwood Park (CA)

(73) Assignee: Gemini Corporation, Calgary, Alberta (CA)

( * ) Notice: Subject to any disclaimer, the term of this patent is extended or adjusted under 35 U.S.C. 154(b) by 281 days.

(21) Appl. No.: 12/491,910

(22) Filed: Jun. 25, 2009

(65) Prior Publication Data

US 2010/0021979 A1    Jan. 28, 2010

Related U.S. Application Data

(60) Provisional application No. 61/075,517, filed on Jun. 25, 2008.

(30) Foreign Application Priority Data

Oct. 17, 2008  (CA) ..................................... 2641270

(51) Int. Cl.
   *C12P 5/02*       (2006.01)
(52) U.S. Cl.
   USPC .............................. 435/167; 435/41; 435/166
(58) Field of Classification Search
   None
   See application file for complete search history.

(56) References Cited

U.S. PATENT DOCUMENTS

| 4,022,665 | A * | 5/1977 | Ghosh et al. ................... 435/167 |
| 5,707,417 | A * | 1/1998 | Yokoyama et al. ................ 71/10 |
| 6,966,989 | B2 | 11/2005 | Hojsgaard et al. |
| 7,101,482 | B2 | 9/2006 | Chauzy et al. |
| 7,311,834 | B2 | 12/2007 | Lee, Jr. |
| 7,332,095 | B2 | 2/2008 | Johnston et al. |
| 2004/0025715 | A1 * | 2/2004 | Bonde et al. .................... 99/485 |

FOREIGN PATENT DOCUMENTS

CA    2641270    5/2012

OTHER PUBLICATIONS

Kirchmayr, R., et al., "Anaerobic Degradation of Animal By-Products", 2007, Chapter 9, pp. 159-191 in "Utilization of By-products and Treatment of Waste in the Food industry", US.

* cited by examiner

*Primary Examiner* — Allison Ford
*Assistant Examiner* — Yvonne Pyla

(57) ABSTRACT

A process and an apparatus for the manufacture of biogas and a solids fraction from an organic waste feedstock is provided. The process involves thermal hydrolysis of the organic waste feedstock at a temperature from about 100 to about 220° C., a pressure from about 5 to about 20 bars, for a period of time from about 15 minutes to 4 hours, to produce a hydrolysate. The hydrolysate undergoes anaerobic digestion at a temperature from about 25 to 60° C., for a period of time from about 1 to 35 days to produce a biogas stream, characterized as having a methane content from between 55 to 75% by volume and a digestate. The digestate is separated into a solids fraction and a liquid fraction, and a portion of the solids fraction is recycled for further anaerobic digestion.

4 Claims, 10 Drawing Sheets

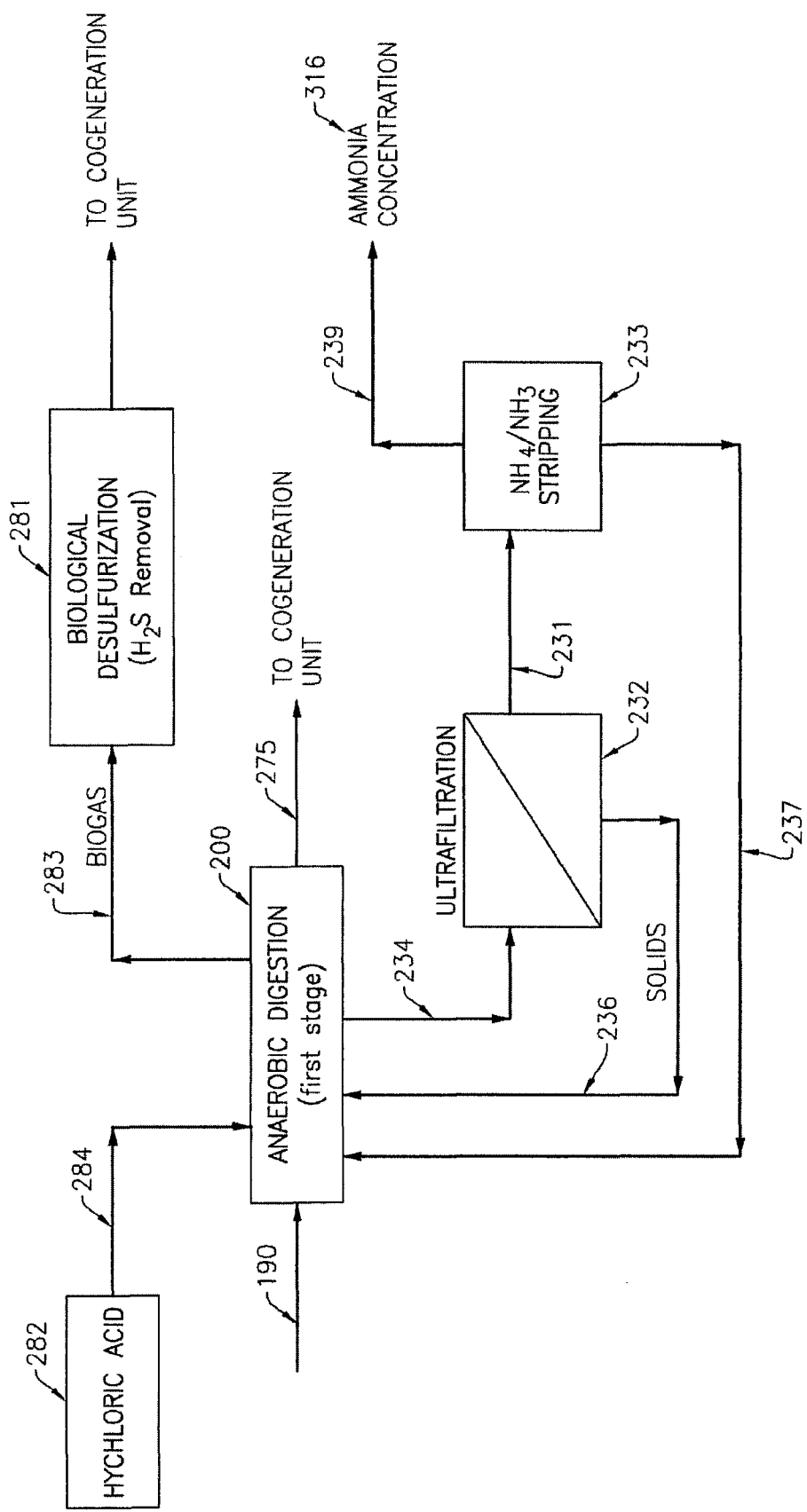
Fig. 2: Process of How to Incorporate Ammonia Stripping into the Digester

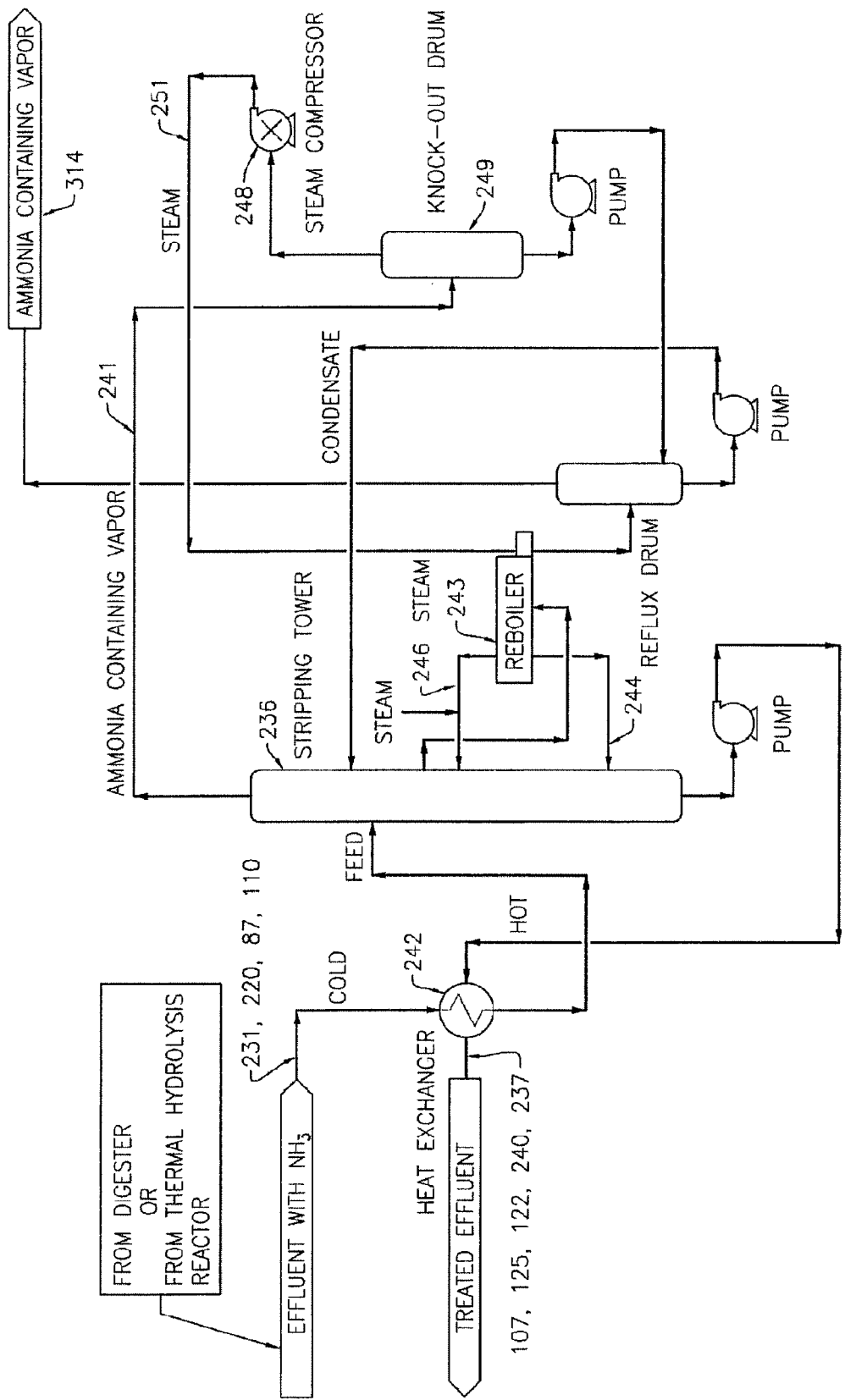
Fig. 3A: Ammonia Removal Process

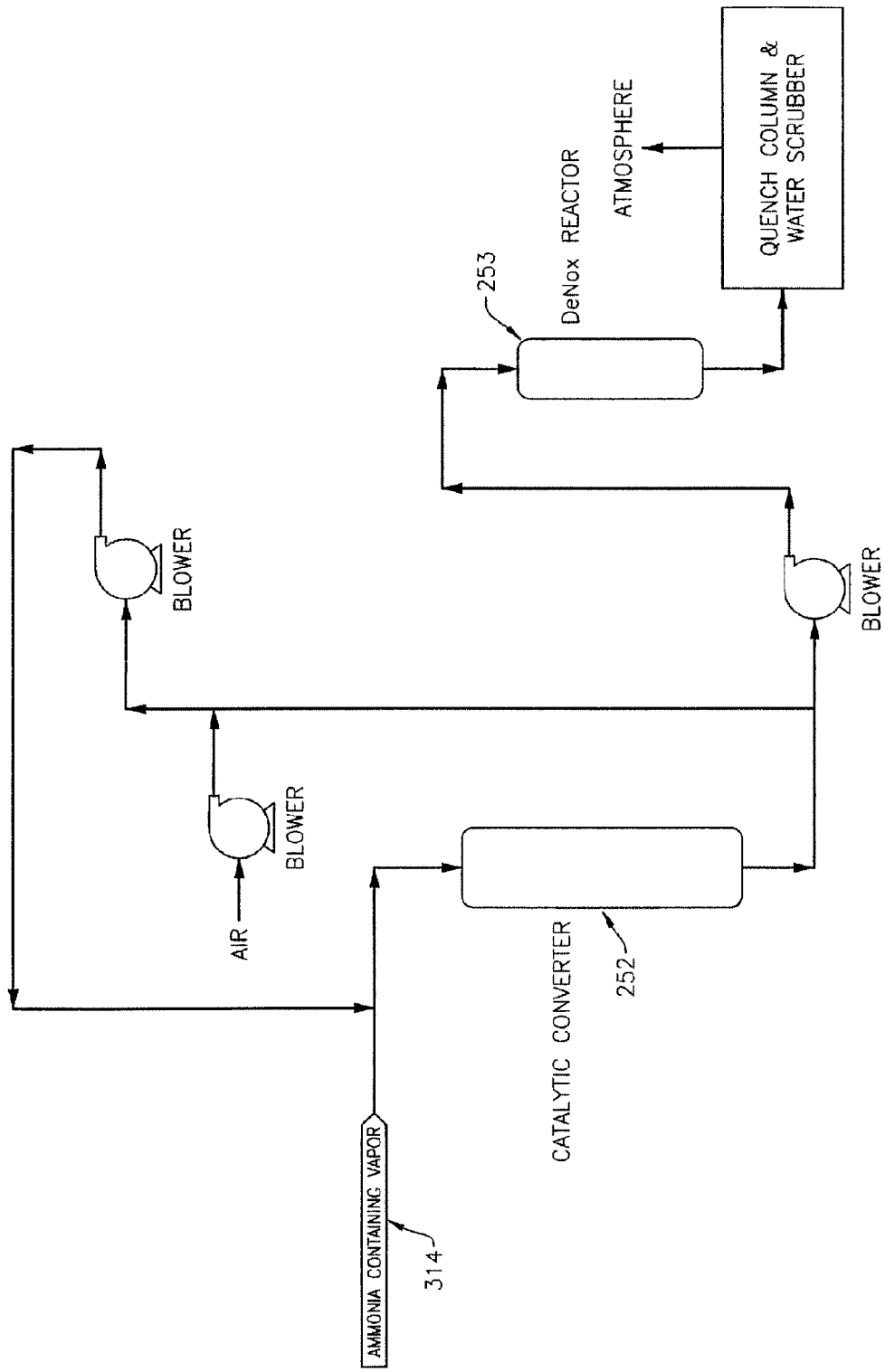
Fig. 3B: Ammonia Removal Process

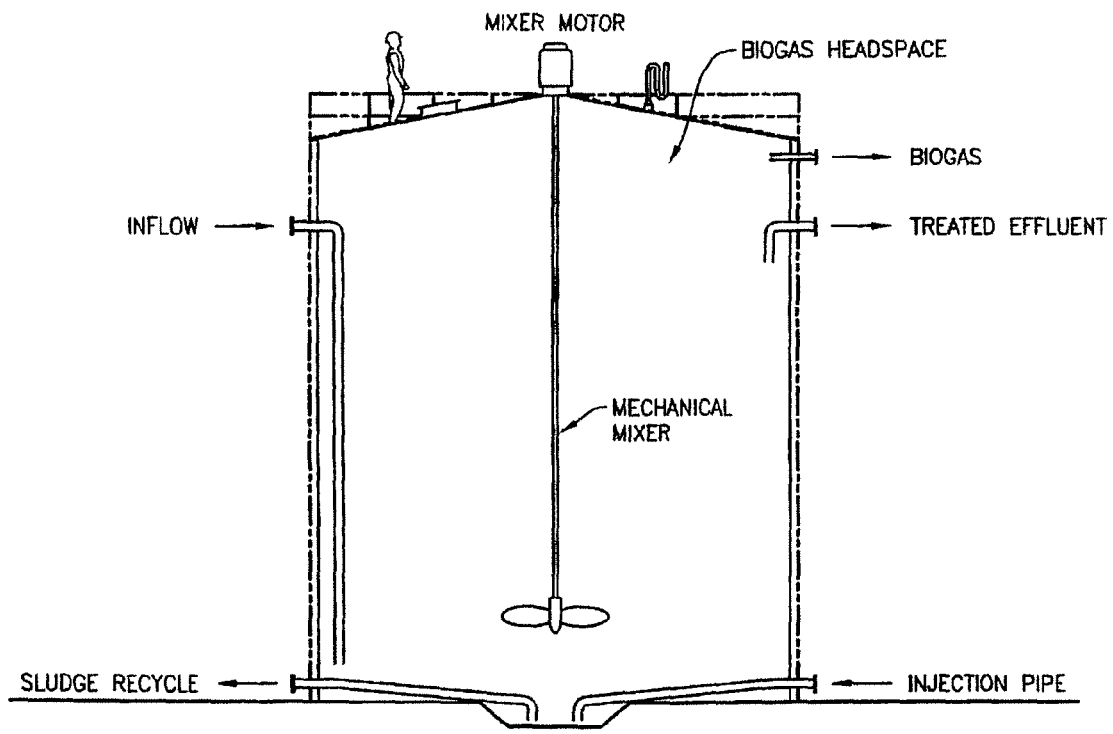
Fig. 4A: Basic Anaerobic Digester with Internal Mixer

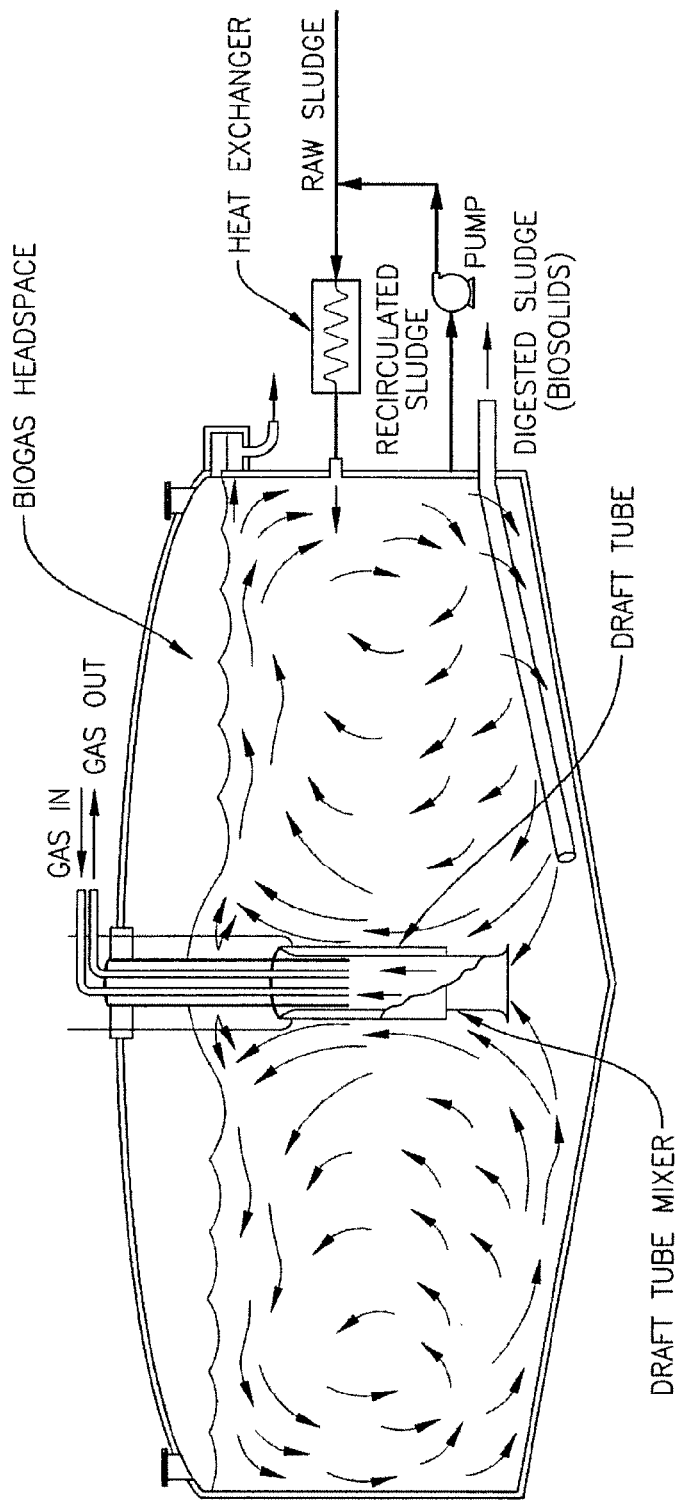
Fig. 4B: Anaerobic Digester with Draft Tube Using Gas Induced Mixing

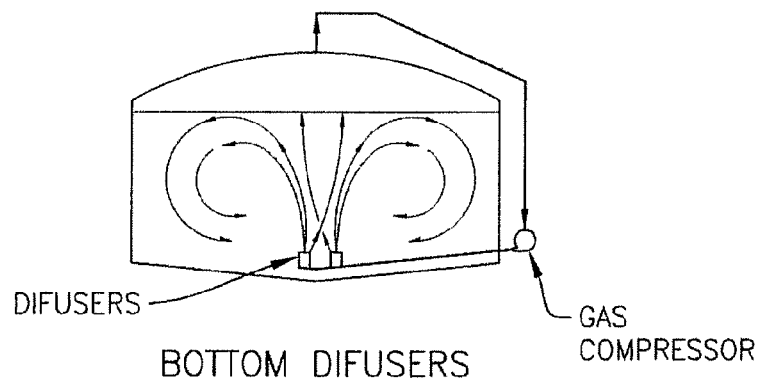
BOTTOM DIFUSERS
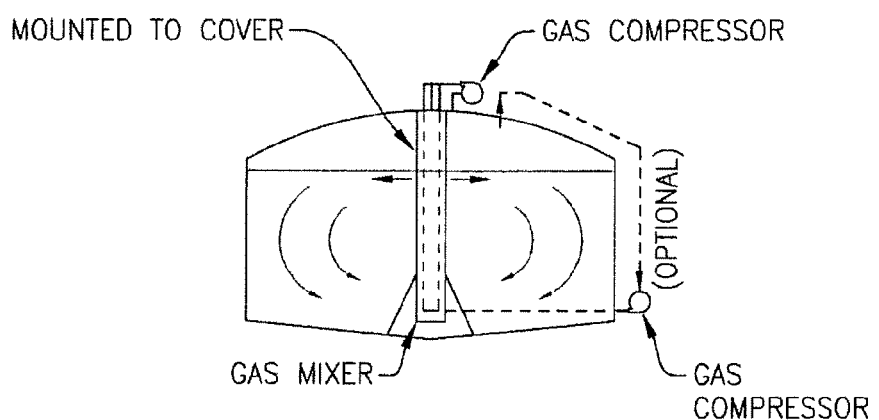
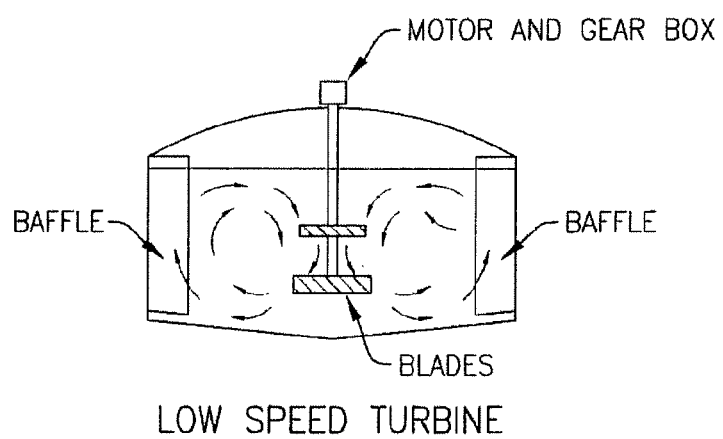
LOW SPEED TURBINE
Fig. 4C1: Example Anaerobic Digester Mixing Systems

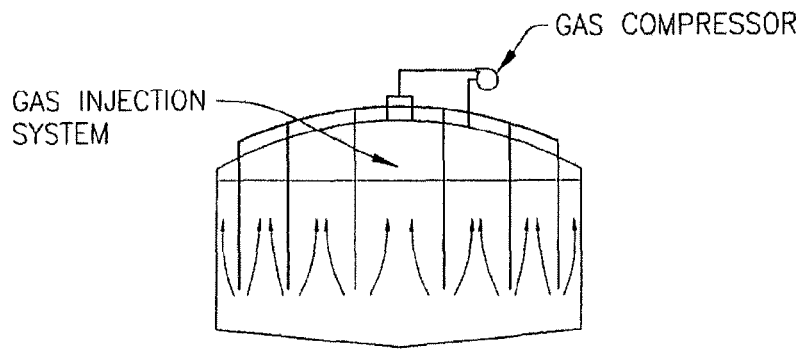
COVER MOUNTED LANCES
(a)
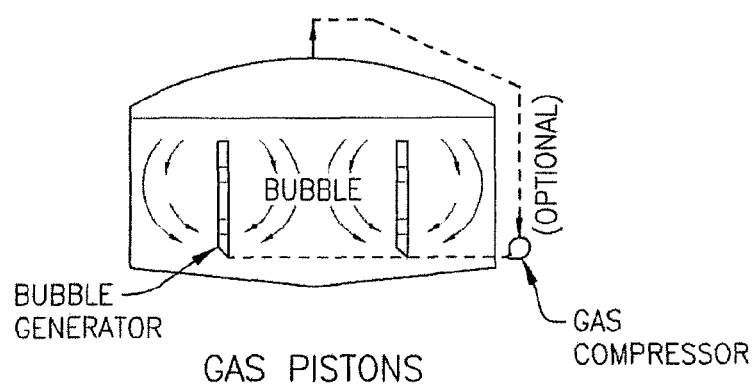
GAS PISTONS
(b)
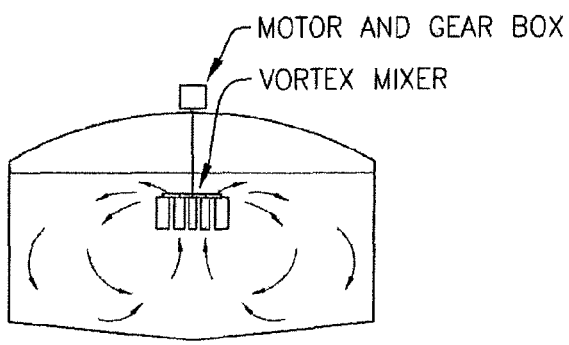
LOW SPEED MIXER
(c)
Fig. 4C2: Example Anaerobic Digester Mixing Systems:
    (a) Unconfined Gas-Injection Systems,
    (b) Confined Gas-Injection Systems,
    (c) Mechanical Stirring Systems,

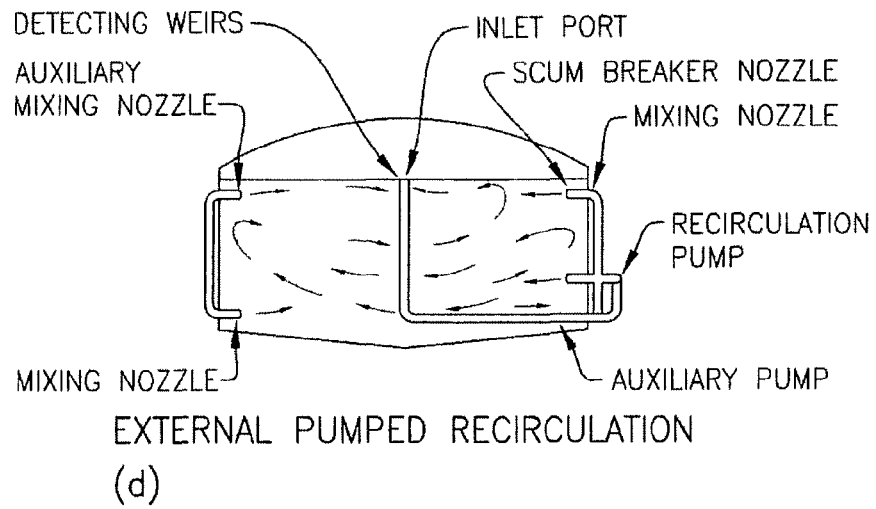
EXTERNAL PUMPED RECIRCULATION
(d)
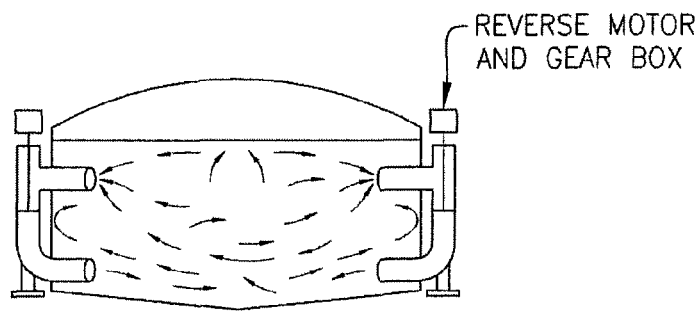
EXTERNAL DRAFT TUBES
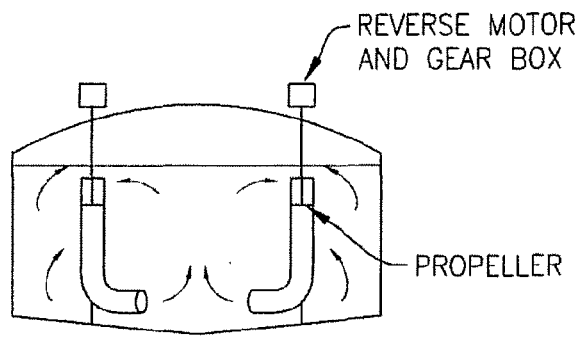
INTERNAL DRAFT TUBES
Fig. 4C3: Example Anaerobic Digester Mixing Systems:
(d) Mechanical Pumping Systems

APPARATUS AND PROCESS FOR PRODUCTION OF BIOGAS

CROSS-REFERENCE TO RELATED APPLICATIONS

This application claims the benefit of U.S. Provisional Application No. 61/075,517 filed Jun. 25, 2008, and also claims the benefit of Canadian Application No. 2,641,270 filed Oct. 17, 2008 which is pending. These applications are herein incorporated in their entirety.

FIELD OF INVENTION

The present invention relates to an apparatus and a process for the production of biogas from biodegradable organic waste.

BACKGROUND OF THE INVENTION

Biogas, principally methane and carbon dioxide, may be produced from feedstocks comprising organic matter, either as a slurry or sludge, for example, sludge from wastewater treatment, treatment of sludge produced in water purification, or treatment of particulate biodegradable organic waste. Processes to produce biogas typically involve the treatment of complex organic material, both the liquid and residual solids fractions, using thermal hydrolysis. Techniques that employ both thermal hydrolysis and anaerobic digestion are directed to the treatment of a limited group of organic material feedstocks, for example wastewater treatment bio-solids.

The treatment of wastewater treatment of bio-solids by thermal hydrolysis and anaerobic digestion produces a carbonaceous material that is reduced in volume compared to the feedstock and may be landfilled, used as a soil additive, or as a fuel to generate energy. However, these processes treat the liquid fraction produced following thermal hydrolysis, are not configured to maximize the manufacture of biogas using anaerobic digestion.

U.S. Pat. No. 7,311,834 teaches an apparatus for the treatment of particulate biodegradable organic waste using thermal hydrolysis and anaerobic treatment. The process uses thermal hydrolysis at a temperature from 130 to 225° C., and at a pressure at or above the saturated water vapor pressure, to produce a solubilized organic material liquid fraction and residual solids. The solubilized organic material is separated from the residual solids, and the solubilized organic material is treated by anaerobic digestion to produce methane rich biogas.

U.S. Pat. No. 7,101,482 discloses a process for treating sludge obtained from biological treatment of effluents for example town or industrial wastewater. The process involves solubilization of the sludge using thermal hydrolysis (between 50° C. and 180° C., and at a pressure between 2 to 40 bars), separation of the liquid and solid fractions using a liquid/solid separator. The separated solids fraction is recycled for further solubilization, while the liquid fraction is treated directly in a biological treatment process for the manufacture of biogas.

U.S. Pat. No. 6,966,989 teaches the use of high pressure, high temperature thermal hydrolysis for treating sludge containing fermentable organic material, for example obtained from urban or industrial wastewaters, or sludges originating from sewage main cleaning operations. The products from thermal hydrolysis (130 to 200° C., and a pressure of between 10 Bar to 20 Bar) may be combined with a mesophilic or thermophilic anaerobic digester for the production of biogas.

U.S. Pat. No. 7,332,095 teaches a method of wet oxidation of organic material obtained from industrial or consumer waste, at an amount of less than 10% (by weight) within the feedstock. The process involves thermal treatment (100 to 300° C. and a pressure between 1.4 to 13 MPa) of the dilute feedstock in presence of a catalyst. The vapour phase is condensed to obtain acetic acid, formic acid and $CO^2$, and the liquid phase is recycled for further thermal treatment.

SUMMARY OF THE INVENTION

The present invention relates to an apparatus and a process for the production of biogas from biodegradable organic waste.

It is an object of the invention to provide an improved apparatus and a process for the production of biogas from biodegradable organic waste.

According to the present invention there is provided a process for manufacture of biogas and a solids fraction from an organic waste feedstock comprising:

i) thermal hydrolysis of the organic waste feedstock at a temperature from about 100 to about 220° C., a pressure from about 5 to about 20 bars, for a period of time from about 15 minutes to 4 hours, to produce a hydrolysate;

ii) anaerobic digestion of the hydrolysate, at a temperature from about 25 to 60° C., for a period of time from about 8 to 35 days to produce a biogas stream and a digestate;

iii) separating the digestate into a solid fraction and a liquid fraction, and recycling the solids fraction to the step of anaerobic digestion (step ii); and iv) obtaining the biogas stream, and the solids fraction, wherein the biogas is characterized as having a methane content from between 55 to 80% by volume.

The present invention pertains to the method described above wherein the step of separating (step iii) is followed by a second anaerobic digestion of the liquid fraction at a temperature from about 25 to 60° C., for a period of time from about 8 to 35 days to produce a second biogas stream and a second digestate comprising a second solid fraction; the biogas stream and second biogas streams, are combined prior to the step of obtaining (step iv).

The present invention provides the process as defined above wherein in the step of thermal hydrolysis (step i), the organic waste feedstock may be selected from the group consisting of animal by-products, specified risk material, food waste, waste water treatment solids, biodegradable municipal sludge, yard waste, and a combination thereof.

The present invention also includes, providing the organic waste feedstock as a coarse particulate material from about 0.01 mm to about 50 mm, in size, and the coarse particulate material is used as the organic waste feedstock for the step of thermal hydrolysis (step i). Alternatively, there is included a step of reducing the particle size of the organic waste feedstock to produce a coarse particulate material from about 0.01 mm to about 50 mm, in size, and the coarse particulate material is used as the organic waste feedstock for the step of thermal hydrolysis (step i).

If there are any metals within the coarse particulate feedstock, then the present invention also provides a process described above that includes a step of metal removal, prior to thermal hydrolysis of the feedstock (step i). Furthermore, if required, the particle size of the coarse particulate material may be further reduced in a second step of reducing particle size, to produce a fine particulate material of from about 0.01 mm to about 10 mm, that is used for the step of thermal hydrolysis.

The present invention also includes the process as described above, wherein the coarse particulate material, the fine particulate material, or a combination thereof, is provided as a slurry at a concentration of about 10% to about 85% (m/m) solids content of the slurry stream. The slurry stream may comprise added water, or the liquid fraction recycled from the step of separating (step iii).

The present invention also provides a process as described above that includes a step of adjusting the C:N ration of the hydrolysate to produce a C:N ratio from about 10:1 to about 30:1 to produce a blended hydrolysate, by adding a balancing organic feedstock, for example but not limited to, manure, organic food waste, or a combination thereof to the hydrolysate produced in the step of thermal hydrolysis (step i). The blended hydrolysate is added to the step of anaerobic digestion (step ii).

The present invention pertains to the process as described above that includes a step of removing nitrogen during the step of anaerobic digestion (step ii) using a nitrogen remover. The step of removing nitrogen may include anaerobic ammonium oxidation, ammonia stripping, ion exchange, or a chemical nitrogen suppressant system.

The biogas and the solids fraction produced according to the process defined above may be used for the production of thermal energy, the solids fraction may be used as a soil amendment, or a combination thereof.

The present invention also provides an apparatus for manufacture of biogas and a solids fraction from an organic waste feedstock comprising:
- a receiving bin for receiving the organic waste feedstock and supplying the organic waste feedstock to a thermal hydrolysis reactor,
- the thermal hydrolysis reactor for processing the organic waste feedstock at a temperature from about 100 to about 220° C., a pressure from about 5 to about 20 bars, for a period of time from about 15 minutes to 4 hours to produce a hydrolysate;
- an anaerobic digester for processing the hydrolysate at a temperature from about 25 to 60° C., for a period of time from about 1 to 35 days to produce the biogas and a digestate;
- a solids thickening tank for separating the digestate into the solid fraction, a liquid fraction, and a biogas fraction, the biogas characterized as having a methane content from between 55 to 80% by volume.

The present invention pertains to the apparatus described above that comprises a second anaerobic digester for processing the liquid fraction obtained from the solids thickening tank, at a temperature from about 25 to 60° C., for a period of time from about 1 to 35 days, or from about 8 to 35 days, to produce biogas and the solid fraction.

The biogas and the solids fraction produced using this apparatus may be used for the production of thermal energy, the solids fraction may be used as a soil amendment, or a combination thereof.

The present invention provides the apparatus above, wherein the organic waste feedstock may be selected from the group consisting of animal by-products, food waste, waste water treatment solids, biodegradable municipal sludge, yard waste, and a combination thereof.

The present invention pertains to the apparatus as described above that further comprises a particle size reducer to produce a coarse particulate material of from about 0.01 mm to about 50 mm. The coarse particle reducer is in operative communication with the thermal hydrolysis reactor.

The present invention also provides the apparatus as defined above that further comprises a metals remover. The metals remover may also be a particle reducer and reduce the particle size of the coarse particulate material to a fine particulate material of from about 0.01 mm to about 10 mm.

The present invention may include an apparatus as described above that comprises a supply of balancing organic feedstock, carbon balancing feedstock, or a combination thereof in operative communication with the anaerobic digester. The apparatus described above may further comprise a nitrogen remover, a chemical nitrogen suppressant system, or both, in operative association with the anaerobic digester.

The process of the present invention may use a range of feedstocks including specified risk material (SRM). Treatment of the feedstock at high temperature, and high pressure thermal hydrolysis, optionally combined with a carbon balancing feedstock system and an optional nitrogen removing system, results in increased yields of biogas production. The treatment of unconventional feedstocks, including animal by-products, comprising SRM, that are not suitable for treatment by anaerobic digestion alone for the manufacture of biogas due to regulatory concerns and inefficient bioconversion of the feedstock within the digester may be processed as described herein.

Without wishing to be bound by theory, the processing of feedstocks, including animal by-products using thermal hydrolysis allows for rapid conversion of the animal by-product biosolids, and lower digesting retention times and reduced solids accumulation within the anaerobic digester.

In prior art systems where nitrogen is not removed during anaerobic digestion, suppression of biogas production is observed. The process described herein that optionally includes a carbon balancing feedstock system and an optional nitrogen removing system, produces higher conversion of the volatile solids matter of animal by-product material into biogas, which can be used in the production of electricity and thermal energy.

The present invention provides a process for the manufacture of biogas and a solids fraction from an animal by-product material, including SRM. The solids fraction produced according to the process described herein, that combines the use of high temperature, high pressure thermal hydrolysis and anaerobic digestion for the manufacture of biogas and solids fraction can be disposed to the environment without restriction or limitations using techniques that are economically sustainable.

When combined with the optional steps of adding a carbon source to achieve a minimum carbon to nitrogen ratio of from about 10:1 to about 30:1, or about 15:1 together with a step of solids thickening and recycling the solids fraction to the anaerobic digester, the process described herein produces increased yield of volatile solids for conversion to biogas when compared to prior art process Biogas production using prior art systems produces yields of about 0.3 to 0.8 Nm3/kg of volatile solids (VS) matter input using a sustained volatile solids loading of between 1.9 to 4.0 kg of VS/(m3 d) (maximum 4.2 kg VS/(m3 d)), for an anaerobic digestion process. Using the system described herein, and using animal by-products as the feedstock, biogas production rates of between about 0.8 to 2.5 Nm3/kg, or any amount therebetween, for example 1.0-1.5 Nm3/kg, of VS matter input using the same sustained volatile solids loading rates are attainable, with the bioconversion rate being about 1.5 to 2.0 times, or any amount therebetween, higher than in existing systems.

Without wishing to be bound by theory, the thermal hydrolysis operates in a manner similar to a heat pump whereby steam condenses onto the organic material providing an efficient means of heat transfer, and upon completion of the process and subsequent venting of the reactor, steam vaporization utilizes latent heat requirements for vaporization to efficiently cool the processed material yet maintaining a slurry composition, before release from the reactor. Unlike other process, the present invention permits high rate anaerobic digestion at temperature ranges from 25 to 60° C. of animal by-product material by way of mechanical simulation of hydrolysis. Employment of thermal hydrolysis in the pre-conditioning of the animal by-products, or any feedstock, increases the conversion rate of the volatile solids that can be achieved biologically. Treatment of the animal by-products by high temperature, high pressure thermal hydrolysis significantly increases the bio-conversion of the volatile solids fraction. For example using animal by-products as a feedstock, the bio-conversion of the volatile solids fraction is anticipated to be in the range of 85 to 95% of the animal by-product volatile solids content based on the hydraulic retention time of the digester. Digestion of animal by-products without pre-treatment by thermal hydrolysis is anticipated to result in bio-conversions equal to or less than 50% of animal by-product volatile solids content.

The present invention also addresses the issue of nitrogen build-up, appearing as ammonia, ammonium, nitrate and nitrite, which can have the effect of suppressing the digestion process when processing feedstock materials comprising of greater than 30% animal by-products.

The process as described herein may process feedstock materials comprising of animal by-products at a percent ratio as high as 85% by mix weight (m/m).

The use of thermal hydrolysis as a feedstock pre-conditioning technology and higher temperatures within the digester allows for smaller capacity digesters, resulting in a lower capital investment and operational expense compared to larger digesters.

This invention relates to a process and an apparatus for the manufacture biogas from high particulate biodegradable organic waste. More particularly, the invention relates to processing of animal by-products, including Specified Risk Material (SRM), in the form of coarse ground material or full carcasses. The hydrolyzed feedstock (hydrolysate) may be combined with a carbon balancing feedstock consisting of food wastes from household and commercial food services, and organic residuals, examples of which include agricultural crops, such as barley seeds and stalk. Animal by-products, which can contain SRM, are normally incinerated or land-filled following the Bovine Spongiform Encephalopathy (BSE) outbreaks, and identification of risks associated with animal consumption of prion infected material, as part of risk mitigation for the transfer of BSE.

The apparatus involves the use of high temperature, high pressure thermal hydrolysis combined with anaerobic digestion for the manufacture of biogas, comprising principally of methane and carbon dioxide, a carbon balancing feedstock system for correction of input material carbon to nitrogen ratio and includes a nitrogen removal system for treatment for the removal of ammonia from the digestate slurry during the process of digestion.

The process described herein is also applicable to the treatment of other complex organic materials, which without pre-treatment by high temperature, high pressure thermal hydrolysis may not be processable by anaerobic digestion alone for the production of biogas in significant volumes and rates.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2 shows a schematic of a process of ammonia stripping and de-sulphurization that may be used with the present invention.

FIGS. 3A and 3B show a schematic of an ammonia removal process that may be used with the present invention.

FIG. 4A-4C3 shows examples of anaerobic digesters that may be used with the present invention.

DETAILED DESCRIPTION

The present invention relates to an apparatus and a process for the production of biogas from biodegradable organic waste.

The following description is of a preferred embodiment.

A process and apparatus for converting organic waste, for example organic waste comprising animal by-products, into biogas using high temperature, high pressure thermal hydrolysis with anaerobic digestion is provided.

Biogas is typically characterized as having a methane content from between 55 to 80% by volume. The remaining balance is $CO_2$ with trace amounts (<1% by volume) of $H_2S$, $N_2$, $H_2$ and ammonia. The methane content of the biogas as produced according to the methods described herein may reside in the upper percentile depending upon the feedstock employed. For example the methane content of biogas produced as described here may range from about 60 to about 80% by volume, or any amount therebetween, for example 60, 62, 64, 66, 68, 70, 72, 74, 76, 78, 80%, by volume or any amount therebetween, when animal by-products are used as feedstock. Animal by-products contain large concentrations of carbohydrates, proteins, and fatty acids. After the long organic chains are broken to smaller organic chains through thermal hydrolysis, acid-forming bacteria ferment the subunits to volatile organic acids, hydrogen and carbon dioxide. These products are biologically converted to hydrogen, carbon dioxide and acetate; which are then consumed and converted by methanogenic bacteria to produce methane and carbon dioxide, or biogas. The presence of fatty acids in the animal by-products contributes to a high methane content in the biogas.

Figure 1A:
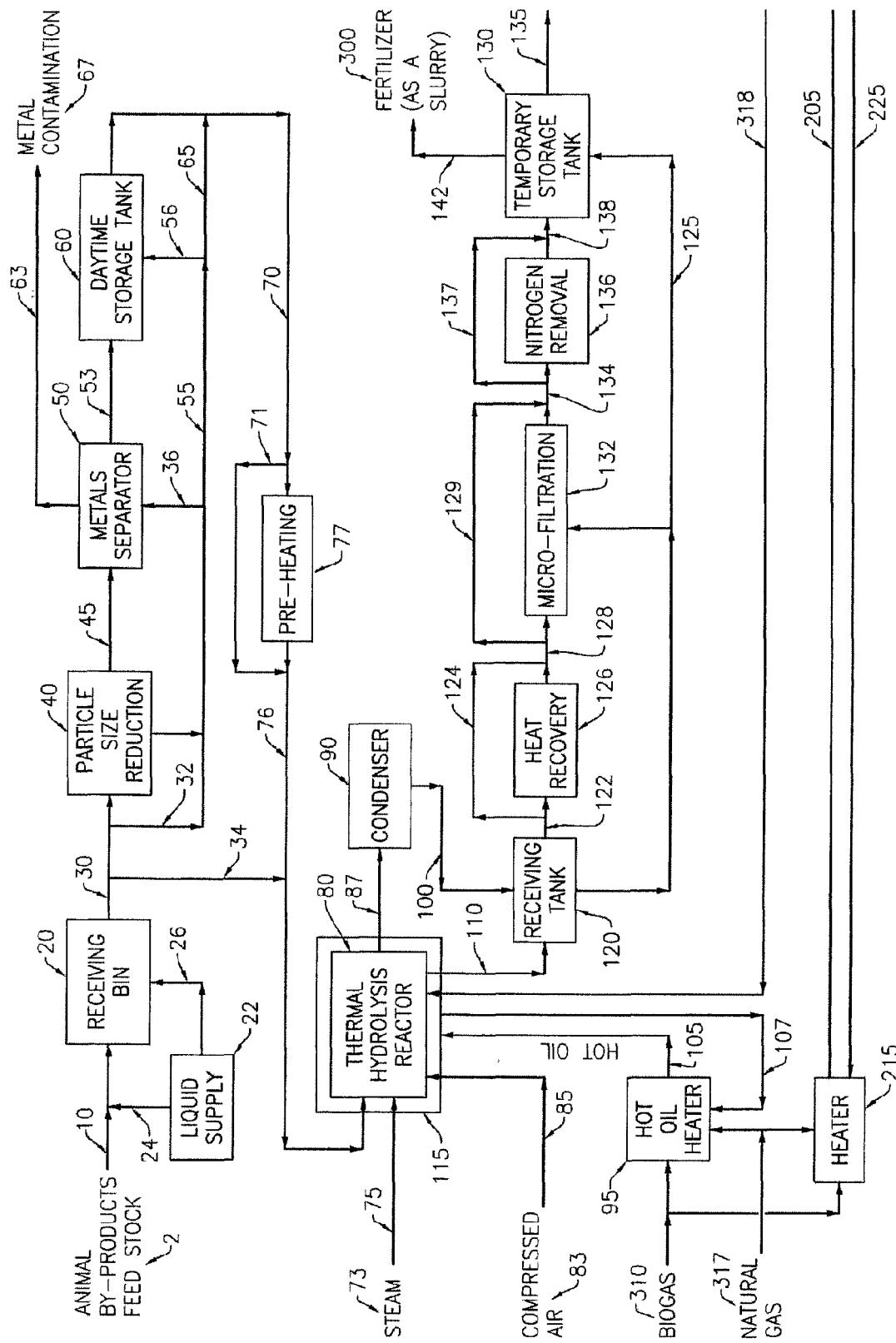
FIG. 1A-1B shows a schematic of the process for treating animal by-products for conversion of the material's volatile solids fraction into biogas in accordance with an embodiment of the present invention.
Figure 1B:
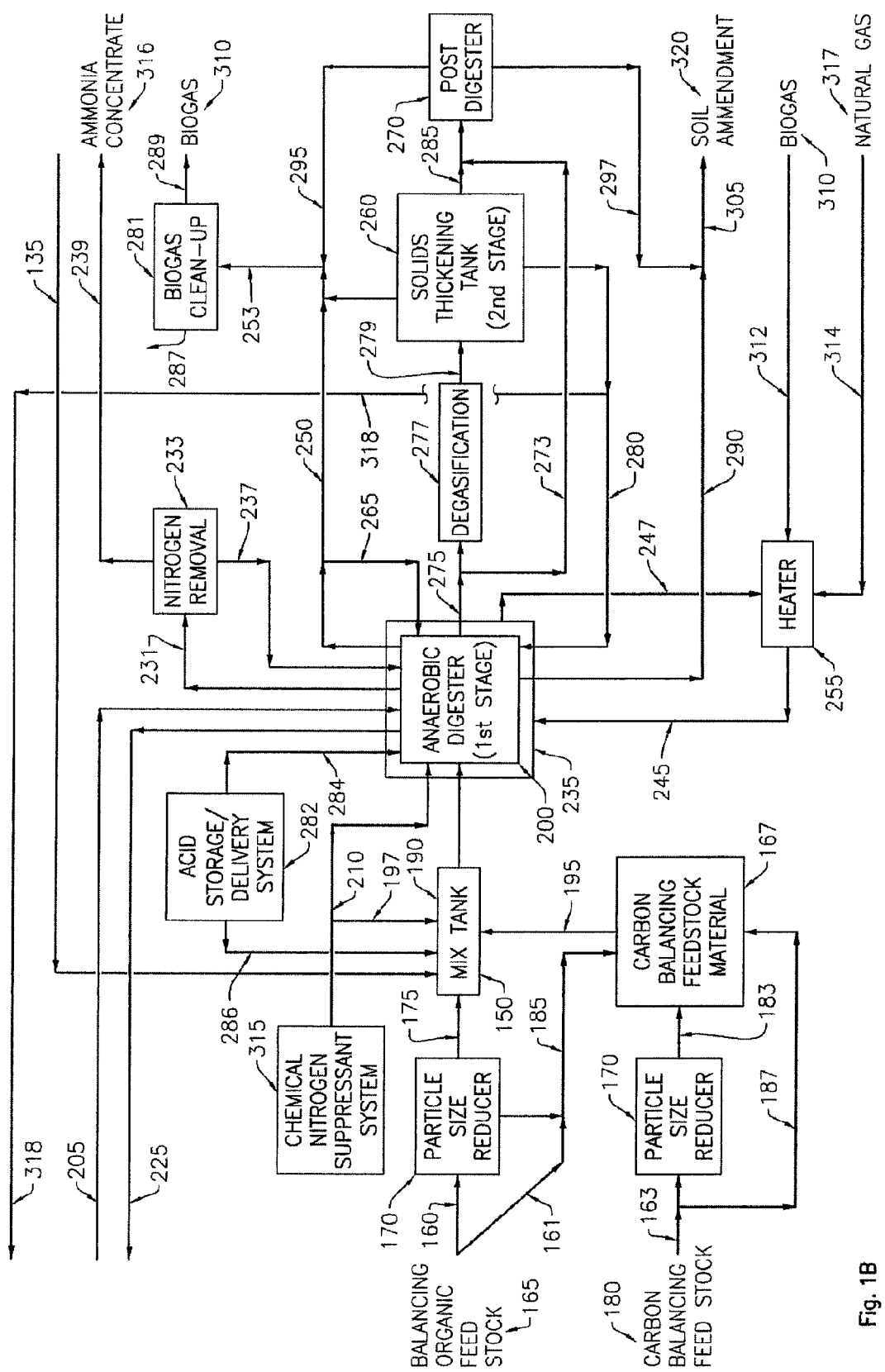

With reference to FIG. 1A-1B, there is shown an overall system for converting organic waste feedstock into biogas. The feedstock 2 may comprise but is not limited to animal by-products, including specific risk material (SRM), food waste, waste water treatment solids, biodegradable municipal sludge, yard waste, or a combination thereof. Any feedstock that is biodegradable may be used according to the method and apparatus as described herein. The process as described herein is capable of processing fine ground material, coarse ground material and full carcasses. Feedstocks that are poorly biodegradable using prior art methods involving an anaerobic digester, can be processed as described herein using a method that comprises pre-treatment by thermal hydrolysis. This step increases biodegradability (bio-conversion of their volatile solids (VS) fraction when transferred to the digester) of the feedstock.

Specified Risk Material (SRM) includes tissues that are obtained from infected animals, for example, BSE-infected cattle. SRM may comprise the skull, brain, trigeminal ganglia, eyes, tonsils, spinal cord and dorsal root ganglia of cattle aged 30 months or older and the distal ileum of cattle of all ages (European Union, *Commission Regulation (EC) No 657/2006* of Apr. 10, 2006. Official Journal of the European Union. See URL:eur-lex.europa.eu/LexUriServ/site/en/oj/2006/1_116/1_11620060429en00090013.pdf). The process, as defined herein, is capable of processing SRM, including processing Category 1 (contains those materials of the highest risk, ie BSE); Category 2 (includes all animal by-products that can be allocated to Category 1; and Category 3 (animal by-products fit for human consumption but are not intended for human consumption). The process described herein may be used for treatment of animal by products that typically have been considered not suitable for biogas production (as described for example by R Kirchmayr, et al., "Anaerobic Degradation of Animal By-Products", Chapter 9, pp. 159-191 in "Utilization of By-products and Treatment of Waste in the Food industry", Springer US).

The feedstock 2 may be ground, particulate material, fine ground material, coarse material, for example, part or full animal carcasses, a slurry comprising coarse or fine ground organic material, or other organic material, that is fed into a truck receiving hopper or bin 20 via conduit 10. The use of smaller particle size of the feedstock will improve heat transfer and reduce reactor warm-up time for the thermal hydrolysis due to increased particle surface area and improved heat distribution within the feedstock and result in increased throughput capacity for the thermal hydrolysis due lower batch cycle time. Longer reactor warm-up batch cycle times of up to 1 hour may be required when treating full carcasses versus 30 minutes for fine ground material.

The truck receiving hopper or bin 20 may be equipped with a series of horizontal screw conveyors, or other conveyors or transport means as would be known in the art, located on, at, or near its bottom that transfers the feedstock via conduit 30 for further processing, for example, to a particle size reducer 40 (via conduit 30), metal separator 50 (via conduit 45), daytime storage tank 60 (via conduit 53 or 55 and 56), or to thermal hydrolysis reactor 80 (via conduits 32, 55, 65, 70, 71, and 76) as required. Feedstock can be additionally preheated 77 prior to processing within the thermal hydrolysis reactor 80 to reduce energy consumption. If the liquid content of the feedstock needs to be increased, for example in the case of using bone-meal or other feedstock, then liquid may be added from a liquid supply 22 to the feedstock (via conduit 24 or 26) to produce a feedstock slurry. Minimizing the amount of slurry water added to the feedstock prior to treatment by thermal hydrolysis reduces the energy input required for heating. Results show that high percent solids of minimal moisture, such as bone-meal, can be successfully treated at slurry concentrations from 50% to 75% by weight, or any amount therebetween. It is desirable to limit the amount of slurry water used in the thermal hydrolysis process.

The particle size reducer 40, may comprise a pre-breaker (for example HAARSLEV, PB15, or Anco-Eaglin Inc, 1045 pre-breaker) as would be known to one of skill in the art to produce a coarse ground particulate material or slurry. The particle size reducer 40 reduces particle size to a size amendable to transport within a piping system, for example from 0.01 mm to about 50 mm, or any amount therebetween, or for example about 25 mm. It is to be understood that if the feedstock 2, is obtained as coarse ground particulate mater, then the particle size reducer may not be required, and the ground particulate matter my be preheated 77 (via conduits 32, 55, 65, 70) and transferred to the thermal hydrolysis reactor 80, or transferred directly to the thermal hydrolysis reactor 80 (via conduit 34 and 76).

An optional metal separator 50 may be used to receive the coarse ground particulate material or slurry, for example via conduit 45, or 32, 56 and 36. The coarse ground material or slurry may be gravity discharged from the pre-breaker of the particle size reducer 40 or the receiving bin 20, into the metal separator 50. The metals separator separates metal contaminants from the particulate feedstock, coarse ground material, or slurry, and may be used to protect downstream equipment. Larger metal particles may be removed by any suitable means including magnetic separation, sieving, manual removal and the like and removed via conduit 63 and the metals collected 67. The remaining feedstock may be crushed by the metal separator to produce fine ground material of about 0.01 mm to about 10 mm, or any amount therebetween, for example 5 mm. It is to be understood that if the feedstock is obtained as a fine ground material or slurry that is metal-free, then the fine ground material or slurry may be transferred directly to the daytime storage tank 60 via conduits 32, 55 and 56, or to the thermal hydrolysis reactor 80, via conduits 34 and 76. Additionally, undigested solids from the solids thickening tank 250 can be recycled in the thermal hydrolysis reactor 80 via conduit 318, where the matter can be retreated for further solubilization of any residual organic matter.

The coarse particulate material, the fine particulate material, or a combination thereof may be provided as a slurry to provide a solids content of about 8 to about 20% by weight solids content, or any amount therebetween, for example from about 10 to about 16% by weight solids content, or any amount therebetween, or for example 8, 10, 12, 14, 16, 18, 20% by weight solids content, or any amount therebetween.

Fine ground material or slurry, with reduced metal content, is removed from the metal separator 50 by a suitable conveyor means, for example a screw conveyor, pump or other conveyor means, for example a belt conveyor, to the daytime storage tank 60, or to the thermal hydrolysis reactor 80 as required. The use of the daytime storage tank 60 may assist in regulating batch processing volumes for thermal hydrolysis. However, alternate storage tanks may be used, for example, the receiving bin 20 may also be used as a storage tank to regulate batch processing volumes if required.

Thermal hydrolysis may take place using a batch operated process, or it may be operated in a continuous manner, for example using a plug flow system fitted with pressurization and depressurization chambers before and after the thermal hydrolysis reactor.

The daytime storage tank 60, may be fitted with a cone bottom, and equipped with an internally mounted material conveyor, for example an incconduitd screw convey, or pump, or the daytime storage tank 60, may be configured to transport the fine ground material or slurry, via conduit 70, 71, and 76, directly to the thermal hydrolysis reactor 80 for high temperature, high pressure treatment. Alternatively the conveyor, for example the screw conveyor, can be configured to feed the fine ground material into the inlet of a pump, for example, a vane style pump, for transfer of the fine ground material to the thermal hydrolysis reactor 80.

The fine ground material or slurry is received by one, or more than one, thermal hydrolysis reactor 80 that is adapted for high temperature (greater than 180° C.), high pressure (minimum 12 bar) thermal hydrolysis processing (for example BIOREFINEX; available from Biosphere Technologies Inc.), via conduits 34, 55, 65, 70, 71, 76, or a combination thereof, and is treated under high temperature, and high pressure. Treatment of the fine ground material or slurry within the thermal reactor is conducted at about 100 to about 220° C., or any temperature therebetween, for example from about 150 to about 200° C., or any temperature therebetween, for example at 100, 120, 140, 160, 180, 200, 220° C., or any temperature therebetween, for example at about 180° C. Thermal hydrolysis is also conducted at about 5 to about 20 bar pressure, or any amount there between, for example, from about 10 to about 15 bar pressure, or any amount therebetween, for example 5, 6, 7, 8, 9, 10, 11, 12, 13, 14, 15 bar pressure, or any amount therebetween, or about 12 bar pressure (about 1,200 kPa). The fine ground material or slurry is processed within the thermal hydrolysis reactor 80 under high temperature and high pressure for a suitable length of time to solubilize the organic feedstock, for example, from about 15 minutes to about 4 hours, any amount therebetween, for example 20 minutes to 2 hours, or any amount therebetween, for example 15, 18, 20, 22, 24, 26, 28, 30, 32, 34, 36, 38, 40, 42, 44, 46, 48, 50, 52, 54, 56, 58, 60 minutes or any amount therebetween, or from about 0.5, 1, 1.5, 2, 2.5, 3, 3.5, 4 hours, or any amount therebetween, for example about 40 minutes in length.

Steam 73, via conduit 75, and compressed air 83, via conduit 85, may be injected into the thermal hydrolysis reactor 80 to provide direct heating of the fine ground material or slurry. Alternatively, a hot oil heater 95, heated by biogas 310, or natural gas 317, or a combination thereof, may be used whereby hot oil is provided via 105 (and returned via conduit 107) to a jacket 115 surrounding the thermal hydrolysis reactor 80 to indirectly heat the fine ground material or slurry within the thermal hydrolysis reactor to the operating temperature as defined above. Compressed air 83 may be directly injected into the reactor via 85 for direct pressurization of the reactor to achieve the operating temperature and operating pressure as defined above.

During processing of the fine ground material or slurry with the thermal hydrolysis reactor 80, proteins denature and any infectious materials are destroyed. In addition, the first stage of anaerobic digestion, hydrolysis, is mechanically simulated within the thermal hydrolysis reactor 80. A biosolid product for example 300, 320, is produced that can be used as a fertilizer, soil amendment, or disposed of within the environment.

The Canadian Food Inspection Agency (CFIA) has indicated that a treated bio-solids product 300 produced from the thermal hydrolysis system described herein can be disposed of without any further restrictions. The material from the thermal hydrolysis reactor can be used as a fertilizer aid in its original slurry form (e.g. 300) or it can be dried using a disc dryer, modified through the addition of additional nitrogen, phosphorous, etc and converted in pellets to produce a fertilizer or soil amendment, for example 300. Alternatively, and as described below, the bio-solids may be blended with other feedstock (e.g. 165, 180) and used as a feedstock into an anaerobic digester for biogas production.

During processing within the thermal hydrolysis reactor 80, under the temperatures and pressures described above, the first stage of anaerobic digestion within the anaerobic digester 200 (described below) may be mechanically simulated thereby allowing greater biosolids utilization by anaerobic bacteria within the anaerobic digester.

The thermal hydrolysis reactor 80 may be operated in batch mode, whereby the reactor is filled, heated and pressurized, following which the temperature and pressure are held constant at the operating condition and for a desired period of time as defined above. The reactor may also be operated in continuous mode, where the reactor is continuously being filled, the heat and pressure of the reactor maintained under conditions as defined above, and the organic material maintained within the reactor for the duration of thermal hydrolysis as defined above, prior to its removal from the reactor.

After, or during, processing of the fine ground material or slurry within the thermal hydrolysis reactor 80, a vapour phase is vented, via 87, to condenser 90. Any solubilized biosolids and remaining liquid material (thermally processed material) within the reactor 80 are transported to a receiving tank 120 via conduit 110. The thermally processed material, consisting of a slurry of solubilized biosolids and liquid material, is termed hydrolysate. Condensate 100 from the condenser 90 may also be transported to receiving tank 120 to dilute the hydrolysate.

The hydrolysate may be transferred from the receiving tank 120 to a temporary storage tank 130, via 125 using a pump or other suitable conveying means. Optionally, the heat may be recovered from the hydrolysate using a heat exchanger 126, via conduit 122. This step may also be passed via conduit 124, and the hydrolysate may be subject to microfiltration 132, via conduit 124 or 128, followed by a step of nitrogen removal 136, via conduit 134. The remaining hydrolysate may then be held in the temporary storage tank 130, via conduit 138. Each of the steps of heat recovery 126, microfiltration 132, nitrogen removal 136, may be bypassed via conduits 124, 125, 129, 137 as required.

The temporary storage tank 130 may be equipped with an internal mechanical mixer configured to periodically or continuously mix the contents of the tank. The hydrolysate may be pumped via 142 directly from the temporary storage tank 130 for use as fertilizer 300, or transferred via to a mix tank 150 via 135, using any suitable means for example a pump.

The mix tank 150 may be equipped with a mechanical mixer configured to mix and blend the hydrolysate with other feedstock material to produce a blended hydrolysate. Other feedstock materials may include for example, balancing organic feedstock 165 (via conduits 160, 161, 175, 185, 195 as required), carbon balancing feedstock material 180 (via conduits 163, 183, 187, 195 as required), or a mixture of the organic feedstock and carbon balancing feedstock 167 (via conduit 195), to produce a blended hydrolysate within the mix tank 150. The particle size of the balancing organic feedstock 165, the carbon balancing feedstock 180, or both, may be reduced if needed using a particle size reducer 170 prior to transport into the mix tank 150.

The balancing organic feedstock 165, and the carbon balancing material feedstock material 180, are rich in carbon and comprise for example manure, organic food waste, food wastes from household and commercial food services, and organic residual materials examples of which include agricultural crops, for example barley seeds and stalk (straw or stover), or a combination thereof. Without wishing to be bound by theory, blending the hydrolysate with feedstock 165, 180, or a combination thereof 167, in mixing tank 150 may be useful to stabilize anaerobic digestion within the anaerobic digester 200. It is preferred that that the hydrolysate is characterized as having a carbon to nitrogen ratio (C:N) of greater than or equal to 12:1, for example, having a C:N ration from about 15:1 to 30:1 or any ratio therebetween, for example 12:1, 13:1, 14:1, 15:1, 16:1, 17:1, 18:1, 19;1, 20:1, 21:1, 22:1, 23:1, 24:1, 25:1, 26:1, 27:1, 28:1, 29:1, 30:1, or any ratio therebetween, or a C:N ration of about 20:1. If the hydrolysate is produced from a feedstock comprising treated animal by-products, then the mix ratio of hydrolysate to balancing organic feedstock 165 may be less than or equal to 85% animal by product input, by mass. At C:N ratios of greater than 30% for the hydrolysate (treated animal by-products), the process may require the use of a processing step that involves nitrogen, ammonia or ammonium removal (233), in order to control pH and CN ratio.

It has been observed that in the absence of managing the C:N ratio within the digester, increased nitrogen levels result in a rapid peak of biogas production, followed by a rapid decrease in biogas production. At higher nitrogen levels the anaerobic digestion process is suppressed and reduced production of biogas and methane content is observed. By keeping the concentration of nitrogen low within the anaerobic digester, complete anaerobic digestion occurs, and higher yields of biogas are produced.

The blended hydrolysate, or the hydrolysate (if no blending is required), is used as an input material via conduit 190 to the anaerobic digester 200. The blended hydrolysate, or the hydrolysate, is transferred from the mix tank 150, for example via pump, to one or more than one anaerobic digester 200.

The anaerobic digester 200 is preferably of a wet digestion type as would be known to one of skill in the art. Non limiting examples of anaerobic digesters that may be used with the present invention are shown in FIGS. 4A-4C3. Biological degradation of the volatile solids associated with the blended hydrolysate, or hydrolysate, can proceed by low rate, or high rate digestion, depending upon the operating temperature of the anaerobic digester 200. The retention time of the material in the digester will vary depending on the rate of digestion, and may be from about 1 to about 35 days in duration or any amount therebetween, for example 1, 2, 3, 4, 5, 6, 7, 8, 9, 10, 12, 14, 16, 18 20, 22, 24, 25, 26, 28, 30, 32, 34, and 35, days, or any amount therebetween, at a temperature of from about 20 to 65° C., or any temperature therebetween, for example 25 to 40° C., or any temperature therebetween, for example 50 to 60° C.

If the digestion process is high rate digestion, the period of time for anaerobic digestion is from about 1 to about 25 days, or any amount therebetween, for example 1, 2, 3, 4, 5, 6, 7, 8, 9, 10, 12, 14, 16, 18 20, 22, 24, 25 days, or any amount therebetween, for example 10 to about 20 days, or any amount therebetween. For high rate digestion, the anaerobic digester is operated at a temperature of from about 40 to about 65° C., or any temperature therebetween, 50 to 60° C., or any amount therebetween, for example 55° C.

If the digestion process is low rate digestion, the period of time for anaerobic digestion is from about 16 to about 35 days, or any amount therebetween, for example 16, 18 20, 22, 24, 26, 28, 30, 32, 34, and 35 days, or any amount therebetween, for example 20 to about 30 days, or any amount therebetween. For low rate digestion, the anaerobic digester is operated at a temperature of from about 20 to about 45° C., or any temperature therebetween, 25 to 40° C., or any amount therebetween, for example 37° C.

The blended hydrolysate, or the hydrolysate, within the anaerobic digester 200 is circulated and mixed with the contents of the anaerobic digester. A portion of the contents of the digester may be removed via conduit 225 and circulated through a heater 215 and returned to the anaerobic digester 200 via conduit 205. Heater 215 may be a spiral heat exchanger or the like, whereby hot water or other heating medium for example oil, is at a temperature of less than or equal to 80° C. Alternatively, the heat of the anaerobic digester 200 may be maintained at a temperature of less than or equal to 80° C., or from about 20 to about 30° C., or about 25° C., using a heating medium supplied from heater 255 to a jacket 235 surrounding the digester 200, by conduits 245 and 247. The heater fuel for heater 255 may be supplied by either biogas 310 (via conduit 312) or natural gas 317 via conduit 314), or a combination thereof.

Circulation of the hydrolysate or blended hydrolysate within the anaerobic digester 200 may be accomplished by mechanical, hydraulic, gaseous means, or a combination thereof. For example, mechanical mixing may be produced using an internally mounted mixer (e.g. FIG. 4A, 4C1-4C3) located on the roof or wall of the digester, and supported by the digester walls. Alternatively, a portion of the contents of the digester may be removed by a pump, and transferred to a series of hydraulic mixing nozzles located at different locations and elevations within the digester. The mixing nozzles may be positioned to induce horizontal and vertical mixing within the digester. Circulation within the digester may also be produced by re-injecting biogas collected from conduit 250 into the digester via conduit 265. For example, the biogas may be injected at the base of a draft tube, and the rising biogas bubbles within the draft tube cause the contents of the digester 200 to circulate (e.g. FIGS. 4B, 4C1-4C3).

Within the anaerobic digester 200, ammonia may be present in the form of the ammonium ion ($NH_4^+$) or as dissolved ammonia gas ($NH_3$). These two forms are in equilibrium with each other depending on the pH and hydrogen concentration. Below the pH 7.2 the hydrogen concentration is sufficiently high that the equilibrium is shifted to the presence of ammonium ions. Between a concentration range of 50 to 200 mg/L of the ammonia nitrogen, the effect on anaerobic digestion is typically beneficial. Between the concentration range of 200 to 1000 mg/L, no adverse effect are observed. Between the concentration range of 1500 to 3000 mg/L and greater, inhibitory effects occur. At higher pH, for example greater than 7.4 to 7.6, the concentration of ammonia gas can become inhibitory. The pH within digester 200 may be maintained in the range from about 6.5 to 7.2, or any pH therebetween, or from about 6.8 to 7.2, or any pH therebetween, or from about 7.0 to 7.2, or any pH therebetween. The pH may be maintained by adding a suitable acid from an acid storage 282, for example, hydrochloric acid, sulphuric acid, phosphoric acid, citric acid or other acid as would be known to one of skill, to the anaerobic digester 200, via conduit 284, the mix tank 150, via conduit 286, or the recycle stream leading back to the digester (e.g. 280; see also FIG. 2).

In addition to ammonia and ammonium, nitrogen within the anaerobic digester 200 may be present as nitrate, nitrite, or a combination of all of these forms of nitrogen. In order to maximize biogas production within the anaerobic digester 200, it is preferred that the C:N ratio is maintained at about 15:1 to about 30:1, for example 20:1. This ratio may be achieved by adding balancing organic feedstock 165, carbon balancing feedstock material 180, or a combination thereof, to the hydrolysate in order to maintain the desired ratio of C:N. Nitrogen levels within the anaerobic digester may also be managed using a nitrogen remover 233, or by adding balancing organic feedstock 165, carbon balancing feedstock material 180, or a combination thereof, in combination with the nitrogen remover 233.

If a nitrogen remover is used, a portion of the mixture within the anaerobic digester 200 is removed via conduit 231 and treated by the nitrogen remover 233, and returned to digester 200 via conduit 237. The nitrogen remover 233 may involve, for example, anaerobic ammonium oxidation, ammonia stripping (236, FIG. 3A), ion exchange, magnesium ammonium phosphate precipitation, or a combination thereof. Anaerobic ammonium oxidation may involve circulating a portion of the hydrolysate or blended hydrolysate, supplied by conduit 231, through an anaerobic process whereby nitrite and ammonium are converted into nitrogen gas (R Kirchmayr, et al., "Anaeorbic Degradation of Animal By-Products", Chapter 9, see pp. 179-181 in "Utilization of By-products and Treatment of Waste in the Food industry", Springer US). Ammonia stripping may take place by circulating a portion of the hydrolysate or blended hydrolysate, supplied by conduit 231 through a stripping tower whereby slurry pH is decreased, air is injected and nitrogen gas is liberated from the slurry (FIGS. 2, 3A and 3B). Ion exchange may take place by using an ammonium selective ion exchanger such as a zeolite, for example, natural mordenite, or a suitable ion exchange resin, for absorption and isolation of nitrogen from a portion of the hydrolysate or blended hydrolysate, supplied by conduit 231. Alternatively, the nitrogen content within the anaerobic digestor 200 may be reduced using a chemical nitrogen suppressant system 315, that is fed to the digester 200 via conduit 210, or mixed with the organic feedstock 165, carbon balancing feedstock 180, or a combination thereof, in mixtank 150 (via conduit 197) and delivered to the anaerobic digester 200 via conduit 190.

Use of an ammonia stripper 236, is shown schematically in FIGS. 3A and 3B. An example of a distilling column suitable for such used is available from JGC Corporation (2-3-1, Minat Mirai, Nishi-ku, Yokohama 220-6001, Japan). The effluent is fed via 231 into the upper section of the ammonia stripper 236. Simultaneously, steam 244 is injected into the lower section of the column. Steam injection together with the use of a reboiler 243 are used to heat the effluent. Ammonia ($NH_3$) is stripped into the steam which exists at the top of the stripper 241 column as a $NH_3$ rich steam, which is then transferred to a steam compressor 248, via a knock out drum 249. At the compressor 248 the steam is reheated by the compressor and used as the heat source (via conduit 251) for the effluent at the reboiler 243. Following heat exchange within the reboiler, the $NH_3$ rich steam 314 is fed to a $NH_3$ catalytic converter 252 and decomposed into nitrogen and steam. NOx is produced in the $NH_3$ catalytic reaction as a by-product and decomposed in a DeNOx reactor 253. Ammonia stripping has removed between 60 to 95% of $NH_3/NH_4$ fraction in the effluent. Ammonia may also be collected as an ammonia concentrate 316 via conduit 239. An ultra-filtration unit 232 (FIG. 2), in fluid communication with anaerobic digester 200, via conduits 234 and 236, may be used forward of nitrogen removal 233, including ammonia stripping to remove any solids that would seek to foul and cause operational problems. These solids would be recycled to the digester 200 via conduit 237.

Ion exchange, may also be used to remove ammonium ions. Any suitable resin may be used for example but not limited to the natural resin, clinoptilotite. Removal rates for ammonium ions range from between 90 to 95%. The process may utilize exchange beds of about 1.5 m depth. The total volume treated between regeneration periods depends on the input ammonium concentration in the effluent and desired finished water quality. Regeneration of the ion-exchange medium may be performed using an alkaline or neutral sodium or calcium salts. Lime or sodium hydroxide will yield a waste stream containing $NH_4OH$ which can be further treated using the stripping process as described above. In the stripping process, stripping of the waste regenerate can be achieved with air or with steam.

Inorganic adsorbent resins may also be used for the removal of ammonium ions, for example but not limited to mordenite, clinoptilolite, zeolite 3A, zeolite 4A, manganese oxides and clay mineral.

Magnesium Ammonium Phosphate Precipitation (MAP) method involves the addition of $Mg^{2+}$, for example, $Mg(OH)_2$, MgO, $MgCl_2*6H_2O$, or other suitable $Mg^{2+}$ ion, to the digester effluent (e.g, 231) to cause the crystallization of ammonium and phosphate.

Biogas produced from the microbiological degradation of volatile solids within the anaerobic digester 200 is collected in the headspace of the digester and collected via conduit 250. The biogas may then be transferred to a biogas clean-up process 287, involving for example hydrogen sulphide removal, siloxane removal, biogas drying and the like.

Hydrogen sulfide within untreated biogas may reach 4,000 to 5,000 ppm v/v. It may be desired to reduced the level of $H_2S$ to less than 100 ppm v/v for down stream utilization, for example for electricity production, or less than 4 ppm, for example, for upgrading to natural gas levels for commercial natural gas substitution. Dry Removal of $H_2S$ may involve the use of iron oxides, for example iron oxide impregnated wood chips (Connelly-GPM Inc., SulfaTreat, or Sulfur-Rite, frm GTP-Merichem) that selectively interact with $H_2S$ and mercaptans. Regenerable iron-oxide based adsorption (for example Media-G2, form ADI International Inc.), zinc oxide for trace removal of $H_2S$ at elevated temperatures (200° C.-400° C.; from Johnson Matthey Catalysts), or alkaline solids such as hydrated lime that react with $H_2S$ (Molecular Products Ltd.), may also be used for this purpose as desired.

Liquid $H_2S$ removal processes may include but are not limited to reacting $H_2S$ with an alkaline compound in solution followed by exposure to iron oxide which reacts to form iron sulfide; regeneration is achieved by aeration converting the sulfide to elemental sulfur (e.g. GTP Merichem). Chelated-iron utilizing iron ions bound to a chelating agent may also be effectively used for liquid $H_2S$ removal (lo-cat; GTP Merichem). Alkaline salts (caustic scrubbing) using hydroxide solutions may be used to neutralize $H_2S$ acid gas (Dow Chemical Company). Alternatively, amines may be used to scavenge $H_2S$ in liquid which (Sulfa-Scrub; $Q^2$ Technologies).

Treatment of $H_2S$ may also take place within the digester, for example, by adding iron chlorides, phosphates and oxides added directly to the digester to bind with $H_2S$ and form insoluble iron sulfides (ESPI Metals), or by introducing a small amount of oxygen into the head space of the digester or biogas storage tank to encourage growth of aerobic bacteria *Thiobacillus*. Alternative biological $H_2S$ removal process may include using biofilters, fixed-film bioscrubbers and suspended-growth bioscrubbers which have added functionality by often removing multiple contaminants from a gas stream; fluidized-bed bioreactors have been tested for simultaneous removal of $H_2S$ and $NH_3$ (e.g. Biorem).

Biogas drying can be achieved for example by removing moisture entrained in biogas through temperature reduction and subsequent condensing of the water, then reheating of biogas to provide a reduced relative humidity (e.g. Flotech, Sweden), compression of the gas thereby increasing the dewpoint within the vessel to condense the moisture, or with the use of an absorbent (Van Air Systems), activated alumina (porous form of aluminum oxide), silica gel, or other adsorbents, for example molecular sieves.

Siloxanes have low solubility in water and high volatility and travel with sludge into anaerobic digesters and volatilize into the biogas. Combustion of siloxanes creates micro-crystalline sand, creating deposits on combustion surfaces and heat exchanger surfaces. Siloxane may be removed using for example, activated carbon (Univar Canada), and may take place after hydrogen sulfide removal. Alternate adsorbents such as silica gel may also be used for siloxane removal (Applied Filter Technology). A typical recommended range of values for residual siloxanes in biogas is 10-20 mg/m$^3$ biogas.

The remaining solids fraction or digestate following anaerobic digestion may either be transferred from the digester 200 by conduit 275, via a pump or by gravity, to a degasifier 277, then to a solids thickening tank 260 via conduit 279, which may also function as a second anaerobic digester in a manner similar to the anaerobic digester 200, or transferred via conduits 273 and 285 to post digester 270, or transferred via conduit 290 and 305 for use for example as a soil amendment 320. Within the solids thickening tank 260, solid fractions separate from the liquid fraction, for example by gravity or other processes as known in the art, for example centrifugation or filtration. The thickened solids fraction may be recycled back to the digester 200 via conduit 280, and/or to the thermal hydrolysis reactor 80 via conduit 318, for further digestion of the solids to maximize biogas production. The liquid fraction from the solids thickening tank 260 is transferred via conduit 285 to one or more than one post digester 270 for additional biogas production in a manner analogous to that used in the (first) anaerobic digester 200.

One or more than one second anaerobic digester (for example 260, 270), may be employed to achieve two-stage digestion. With this arrangement, the first anaerobic digester 200 is coupled in series with one or more second tank (digester 260 and/or 270) which may or may not be heated. Additional biogas is produced in the one or more second tank. The amount of biogas produced in the second digester is typically less than 20% of total biogas produced, and may vary depending upon the feedstock used.

Biogas produced in the anaerobic digester 200 is transported under low pressure via conduit 250, 253 and 289 for biogas utilization 310. Any additional biogas produced in the post digester 270 is removed via conduit 295 and may be introduced into conduit 250, for biogas utilization 310. Any biosolids remaining after digestion from the anaerobic digester 200 (via conduit 290) or the post digester 270 (via conduit 297), may be utilized as soil amendment. Biogas cleanup 281 utilized to treat and prepare the biogas for utilization, will generate a small waste stream 287 that can be utilized within the process (e.g. returned to the anaerobic digester 200), or combined with the digested solids 300 or 230 for land application.

Using the process and apparatus described above, biogas comprising from about 55 to about 75% methane by weight of the total biogas produced, can be obtained from an organic feedstock comprising animal by-products. The volume and rate of biogas produced from the digestion of animal by-products, that are pre-treated by thermal hydrolysis at high temperature, high pressure as described above is greater than if animal by-products are processed directly by anaerobic digestion alone.

Using the apparatus and method as described herein, bioconversion of the volatile solids (VS) content of animal by-products pre-treated by high temperature high pressure thermal hydrolysis, is from 85% to 95% during anaerobic digestion, and represents an increase in biogas production of between 0.8 to 2.5 times of the amount produced for the input VS matter in comparison to systems that do not employ thermal hydrolysis. For example, unprocessed animal by-products that have not pre-treated by high temperature and high pressure thermal hydrolysis, exhibit a bioconversion of the VS from 40% to 55%, with 1 kg of VS matter destroyed producing approximately 1 N m$^3$ of biogas.

As described above, the thermal hydrolysis of the organic feedstock ensures that any bioactive organisms present within the feedstock, for example specific risk material (SRM), are inactivated and degraded. As a result the process described herein is useful for treating SRMs to produce a biogas and a solid product that have further utility without requiring additional treatment, for example as an energy source, soil amendment, landfill, or a combination thereof.

Therefore, the present invention provides a process for manufacture of biogas and a solids fraction from an organic waste feedstock comprising:

i) thermal hydrolysis of the organic waste feedstock at a temperature from about 100 to about 220° C., a pressure from about 5 to about 20 bars, for a period of time from about 15 minutes to 4 hours to produce a hydrolysate;

ii) anaerobic digestion of the hydrolysate, at a temperature from about 25 to 60° C., for a period of time from about 8 to 35 days to produce a first biogas stream and a digestate;

iii) separating the digestate into a first solid fraction and a liquid fraction, and recycling the first solids fraction to the step of anaerobic digestion (step ii);

iv) optionally, a second anaerobic digestion of the liquid fraction, at a temperature from about 25 to 60° C., for a period of time from about 8 to 35 days to produce a second biogas stream and a second digestate comprising a second solid fraction may take place; and v) combining the first and second (if carried out) biogas streams to produce the biogas, wherein the biogas is characterized as having a methane content from between 55 to 80% by volume, and combining the first and second solids fraction to produce the solids fraction.

The biogas and the solids fraction produced may be used for the production of thermal energy, the solids fraction may be used as a soil amendment, or a combination thereof. The organic waste feedstock may be selected from the group consisting of animal by-products, food waste, waste water treatment solids, biodegradable municipal sludge, yard waste, and a combination thereof.

The process described above may include a step of reducing the particle size of the organic waste feedstock to produce a coarse particulate material, or the feedstock may be provided as a coarse particulate material of from about 0.01 mm to about 50 mm, in size. If there are any metals within the coarse particulate feedstock, then the process described above may include a step of metal removal, prior to thermal processing of the feedstock. Furthermore, if required, the particle size of the coarse particulate material may be further reduced in a second step of reducing particle size, to produce a fine particulate material of from about 0.01 mm to about 10 mm, that that is used for the step of thermal hydrolysis. The coarse particulate material, the fine particulate material, or a combination thereof may be provided as a slurry as described above.

The process described above may also include a step of adjusting the C:N ration of the hydrolysate to produce a C:N ratio from about 10:1 to about 30:1 to produce a blended hydrolysate. The step of producing a blended hydrolysate involves adding a balancing organic feedstock manure, organic food waste, or a combination thereof to the hydrolysate produced in the step of thermal hydrolysis (step i). The blended hydrolysate may be added to the step of anaerobic digestion (step ii).

The process described above may further include a step of removing nitrogen during the step of anaerobic digestion (step ii). The step of removing nitrogen may include the use of a nitrogen remover involving anaerobic ammonium oxidation, ammonia stripping, ion exchange, or a chemical nitrogen suppressant system.

The present invention also provides an apparatus for manufacture of biogas and a solids fraction from an organic waste feedstock comprising:

a receiving bin for receiving the organic waste feedstock and supplying the organic waste feedstock to a thermal hydrolysis reactor, the thermal hydrolysis reactor for processing the organic waste feedstock at a temperature from about 100 to about 220° C., a pressure from about 5 to about 20 bars, for a period of time from about 15 minutes to 4 hours to produce a hydrolysate;

an anaerobic digester for processing the hydrolysate, at a temperature from about 25 to 60° C. or any temperature therebetween, for a period of time from about 1 to 35 days, or any time therebetween to produce the biogas and a digestate;

a solids thickening tank for separating the digestate into the solid fraction and a liquid fraction;

a second anaerobic digester may optionally be used for processing the liquid fraction, at a temperature from about 25 to 60° C. or any temperature therebetween, for a period of time from about 1 to 35 days, or any time therebetween to produce biogas and the solid fraction.

The biogas and the solids fraction produced using this apparatus may be used for the production of thermal energy, the solids fraction may be used as a soil amendment, or a combination thereof. The organic waste feedstock may be selected from the group consisting of animal by-products, food waste, waste water treatment solids, biodegradable municipal sludge, yard waste, and a combination thereof.

The apparatus described above may include a particle size reducer to produce a coarse particulate material of from about 0.01 mm to about 50 mm, that is used as a feed for the thermal hydrolysis reactor. If there are any metals within the coarse particulate feedstock, then the apparatus described above may include metals remover. The metals remover may also be a particle reducer and reduce the particle size of the coarse particulate material to a fine particulate material of from about 0.01 mm to about 10 mm.

The apparatus described above may also include a supply of balancing organic feedstock, carbon balancing feedstock, or a combination thereof to be added to the hydrolysate.

The apparatus described above may further comprise a nitrogen remover, a chemical nitrogen suppressant system, or both, in operative association with the anaerobic digester.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A process for manufacture of biogas and a solids fraction from an organic waste feedstock comprising:

i) thermal hydrolysis of the organic waste feedstock at a temperature from about 100 to about 220° C., a pressure from about 5 to about 20 bars, for a period of time from about 15 minutes to 4 hours, to produce a hydrolysate;

ii) combining the hydrolysate with an external balancing organic feedstock material or an external carbon balancing feedstock material to produce a blended hydrolysate to achieve a carbon:

nitrogen ratio from about 12:1 to 30:1;

iii) anaerobic digestion of the blended hydrolysate at a temperature from about 25 to 60° C., for a period of time from about 1 to 35 days to produce a biogas stream and a digestate;

iv) separating the digestate into a solids fraction and a liquid fraction, and recycling a portion of the solids fraction to the step of anaerobic digestion (step iii);

v) recovering the biogas stream characterized as having a methane content from between 55 to 75% by volume, and the solids fraction.

2. The process of claim 1, wherein the step of separation (step iv) is followed by:

a) a second anaerobic digestion of the liquid fraction at a temperature from about 25 to 60° C., for a period of time from about 1 to 35 days to produce a second biogas stream and a second digestate comprising a second solid fraction, b) combining the biogas stream and the second biogas stream to produce the biogas, and combining the solids fraction from step v) with the second solids fraction to produce a total solids fraction.

3. The process of claim 1, wherein, in the step of thermal hydrolysis (step i), the organic waste feedstock is specified risk material or other organic waste material.

4. The process of claim 3, wherein, the organic waste feedstock is specified risk material.

\* \* \* \* \*